US00PP36448P2

(12) United States Plant Patent
Layt

(10) Patent No.: US PP36,448 P2
(45) Date of Patent: Feb. 11, 2025

(54) ***PHORMIUM* PLANT NAMED 'PHOS6'**

(50) Latin Name: ***Phormium tenax* x *cookianum***
Varietal Denomination: PHOS6

(71) Applicant: Ozbreed Green Life PTY Ltd, Richmond (AU)

(72) Inventor: Todd Layt, Richmond (AU)

(73) Assignee: Ozbreed Green Life Pty Ltd (AU)

( * ) Notice: Subject to any disclaimer, the term of this patent is extended or adjusted under 35 U.S.C. 154(b) by 0 days.

(21) Appl. No.: 18/621,194

(22) Filed: Mar. 29, 2024

(51) Int. Cl.
*A01H 5/12* (2018.01)
*A01H 6/00* (2018.01)

(52) U.S. Cl.
USPC ..... Plt./373

(58) Field of Classification Search
USPC ..... Plt./373
See application file for complete search history.

(56) References Cited

U.S. PATENT DOCUMENTS

PP25,571 P2 * 5/2015 Turner ..... A01H 6/00
Plt./373

* cited by examiner

*Primary Examiner* — Karen M Redden
(74) *Attorney, Agent, or Firm* — Cassandra Bright

(57) ABSTRACT

A new and distinct *Phormium* cultivar named 'PHOS6' is disclosed, characterized by solid green evergreen foliage. Plants remain evergreen in high temperatures, not going summer dormant. *Phytophthera* resistance has been observed in the new variety as well as tolerance for high rainfall, flooding and drought when established. Mature plant size of approximately 35 cm to 40 cm tall and 35 to 40 cm wide. Plants grow vigorously yet remain low-growing, useful for low maintenance landscaping. Plants are suitable for gardens, container cultivation and landscaping. The new variety is a *Phormium*, typically produced as an outdoor ornamental plant.

2 Drawing Sheets

Latin name of the genus and species: *Phormium tenax* x *cookianum*.

Cultivar denomination: 'PHOS6'.

BACKGROUND OF THE INVENTION

The new cultivar is a product of chance discovery. The new cultivar was discovered as a naturally occurring whole plant mutation of the commercial cultivar *Phormium tenax* x *cookianum* 'PHOS2', U.S. Plant Pat. No. 20,249. The selection was made at a commercial nursery during 2017 in New South Wales, Australia.

Asexual reproduction of the new cultivar 'PHOS6' was first performed at a commercial nursery in New South Wales, Australia by vegetative divisions in 2017. Subsequent propagation by cutting and tissue culture has shown that the unique features of this cultivar are stable and reproduced true to type. Approximately fifteen generations have been reproduced.

The following traits have been repeatedly observed and are determined to be the unique characteristics of 'PHOS6'. These characteristics in combination distinguish 'PHOS6' as a new and distinct *Phormium* cultivar:

1. Solid green foliage.
2. Mature plant size of approximately 35 to 40 cm tall and 35 to 40 cm wide.
2. Vigorous plants.
3. Tolerant of climatic extremes, in particular high rainfall and flooding.
4. Resistance to the disease *Phytophthora*.
5. Low growth is attractive for use as a ground cover.
6. Low maintenance in the landscape.

7. Humidity, wind and coastal tolerant.
8. Drought resistant once established.
9. Evergreen; many *Phormium* varieties are summer dormant or die off in high summer temperatures).

PARENT COMPARISON

Plants of the new cultivar 'PHOS6' are similar to the parent in most horticultural characteristics. The new cultivar, however, differs in the following:

1. The new cultivar produces solid green colored foliage; the parent cultivar has solid bronze foliage.
2. Plants of the new cultivar are *Phytophthora* resistant; plants of the parent cultivar are sensitive to *Phytophthora*.
3. Foliage of the new cultivar is sturdier, more leathery than foliage of the parent cultivar.

COMMERCIAL COMPARISON

'PHOS6' can be compared to compared to the commercial cultivar *Phormium tenax* x *cookianum* 'PHOS4', unpatented. Plants of 'PHOS4' are similar to plants of 'PHOS6' in most horticultural characteristics, however, plants of 'PHOS6' differ in the following:

1. The new cultivar produces solid green colored foliage; this comparator produces foliage which is bronze with lime green variegation.

BRIEF DESCRIPTION OF THE PHOTOGRAPHS

Figure 1:
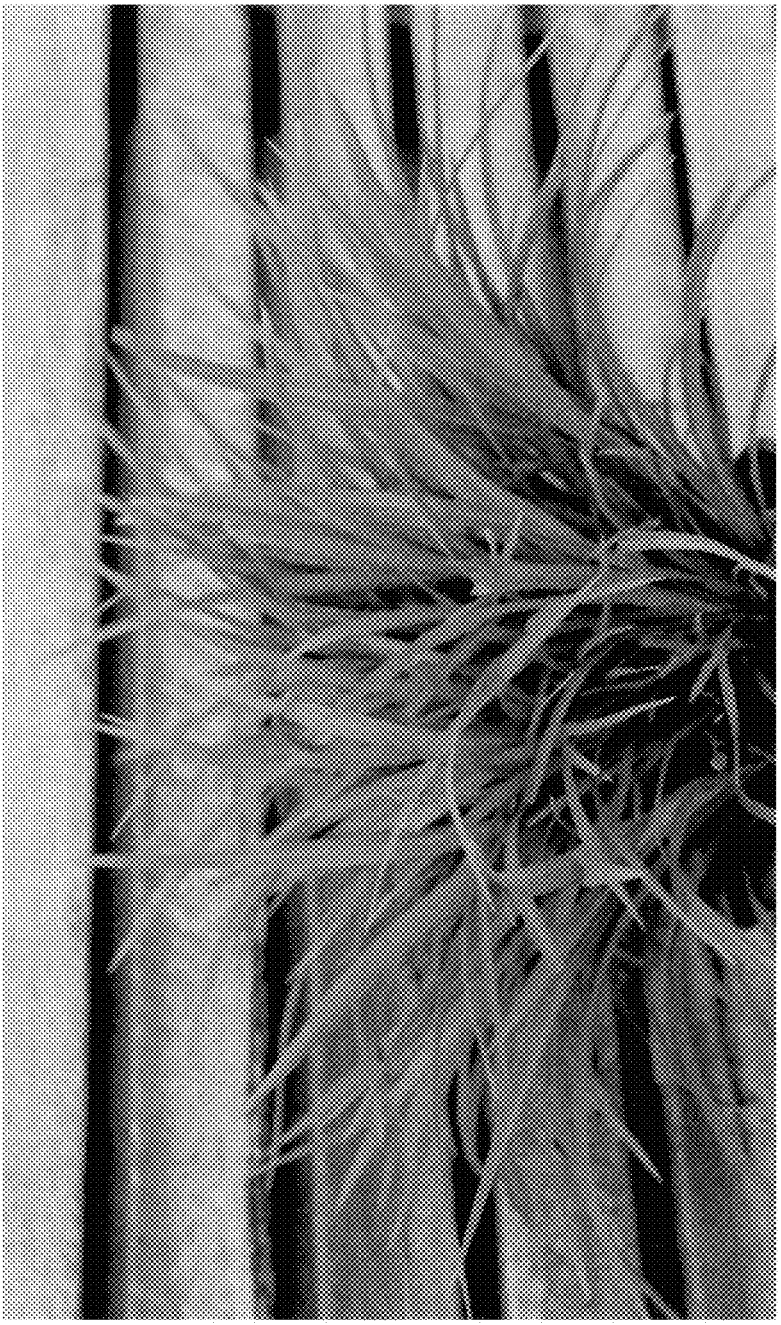

The accompanying drawing in FIG. 1 illustrates in full color a typical plant of 'PHOS6' grown outdoors in Whenuapai, New Zealand. This plant is approximately 12 months old, in a 20 cm pot.

Figure 2:
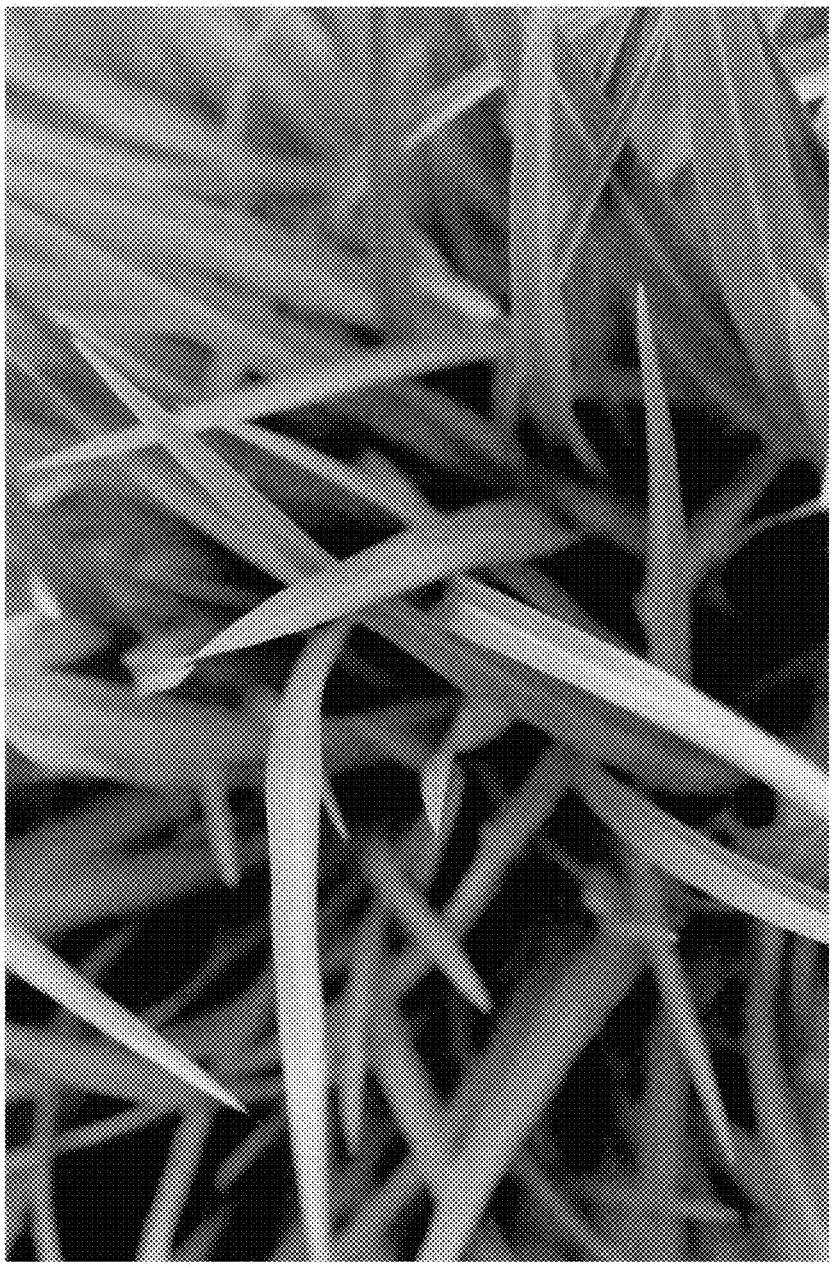

FIG. 2 illustrates a close-up view of typical foliage.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2007, except where general terms of ordinary dictionary significance are used. The following observations and measurements describe 'PHOS6' plants grown outdoors in Dayton, OR. Temperatures ranged from about −2° C. to 8° C. at night to 5° C. to 28° C. during the day. No artificial light, photoperiodic treatments were given to the plants. Measurements and numerical values represent averages of typical plant types.

Botanical classification: *Phormium tenax* x *cookianum* 'PHOS6'.

PROPAGATION

Type of propagation typically used: Division.

PLANT

Growth habit: Upright, evergreen perennial.
Plant shape: Inverted triangle.
Height: Approximately 35 to 40 cm.
Plant spread: Approximately 35 to 40 cm.
Branching characteristics: Herbaceous shoots emerging basally.
Number of clumps per plant: Approximately 10 to 15 distinctive basal clumps, growing very densely together, in an approximately 12-month old plant.
Age of plant described: Approximately 12-months.

FOLIAGE

Leaf:

*Arrangement*.—Cauline.
*Compound or single*.—Single.
*Quantity of leaves per clump*.—8 to 20.
*Average length*.—Approximately 35 cm.
*Average width*.—Approximately 9.3 mm.
*Shape of blade*.—Linear.
*Aspect*.—Upright to slightly arching.
*Apex*.—Acuminate.
*Base*.—Cuneate.
*Margin*.—Entire.
*Texture of top surface*.—Glabrous, finely ridged.
*Texture of bottom surface*.—Glabrous, finely ridged.
*Appearance*.—All surfaces matte.
*Color*.—Young foliage upper side: Near R.H.S. Green 138A, slightly flushed 139C. Young foliage under side: Near R.H.S. Green 138A, slightly flushed 139C. Mature foliage upper side: Near R.H.S. Green 138A, slightly flushed 143C. Mature foliage under side: Near R.H.S. Green 138A, slightly flushed 143C.
*Venation*.—Type: Parallel with 1 prominent, thin midvein. Width of mid vein: Approximately 1 to 2 mm. Venation coloration upper side: Indistinguishable from leaf blade. Venation coloration under side: Indistinguishable from leaf blade.

Petiole: Not present.

FLOWER

Not observed to date.

REPRODUCTIVE ORGANS

Not observed to date.

OTHER CHARACTERISTICS

Disease resistance: Resistant to *Phytophthora*. Neither resistance nor susceptibility to other normal diseases and pests of *Phormium* have been observed.
Drought tolerance and cold tolerance: Tolerates temperatures just below 0° C. to 40° C. and can tolerate slight drought.
Fruit/seed production: Not observed.

What is claimed is:

1. A new and distinct cultivar of *Phormium* plant named 'PHOS6' as herein illustrated and described.

* * * * *